(12) United States Patent
Mondal et al.

(10) Patent No.: US 11,952,657 B2
(45) Date of Patent: Apr. 9, 2024

(54) STAIN HIDING FABRIC WITH METALLIC COATING

(71) Applicant: Milliken & Company, Spartanburg, SC (US)

(72) Inventors: Rajib Mondal, Greer, SC (US); Matthew I. Foote, Spartanburg, SC (US); Gregory A. Satterfield, II, Pelzer, SC (US); Cristina M. Acevedo, Greer, SC (US); Geoffrey R. Haas, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 317 days.

(21) Appl. No.: 16/852,485

(22) Filed: Apr. 19, 2020

(65) Prior Publication Data

US 2020/0370171 A1 Nov. 26, 2020

Related U.S. Application Data

(60) Provisional application No. 62/851,683, filed on May 23, 2019.

(51) Int. Cl.
*D04B 1/16* (2006.01)
*C23C 16/06* (2006.01)
(Continued)

(52) U.S. Cl.
CPC .............. *C23C 16/06* (2013.01); *C23C 16/50* (2013.01); *D04B 1/16* (2013.01); *D06M 11/83* (2013.01);
(Continued)

(58) Field of Classification Search
CPC . D06M 11/83; D06M 16/00; D10B 2509/022; A61K 33/38; A61L 15/18; A61L 2300/104; A61F 2013/00234
See application file for complete search history.

(56) References Cited

U.S. PATENT DOCUMENTS 2,934,066 A 4/1960 Stowasser
3,922,888 A * 12/1975 Patterson ............... D04B 21/06
D5/47

(Continued)

FOREIGN PATENT DOCUMENTS

CN 108251779 A 7/2018
EA 201201638 A1 * 6/2014
(Continued)

OTHER PUBLICATIONS

"JPH10110257_Machine Translation" is a machine translation of JP H10-110257A. (Year: 1998).*
(Continued)

*Primary Examiner* — Larissa Rowe Emrich
(74) *Attorney, Agent, or Firm* — Brenda D. Amidon

(57) ABSTRACT

This invention relates to a method for hiding stains in medical dressings and other textile substrates. The method includes applying a metallic silver coating to a textile substrate via a plasma enhanced chemical vapor deposition (PECVP) process. The metallic silver coating effectively hides any stain that comes into direct contact with the treated substrate by transferring the liquid beneath the surface of the coating. The invention also relates to textile substrates containing metallic silver coatings.

14 Claims, 4 Drawing Sheets

(51) Int. Cl.
  *C23C 16/50* (2006.01)
  *D06M 11/83* (2006.01)
  *D06M 16/00* (2006.01)
  *D06M 23/06* (2006.01)
  *D06M 101/32* (2006.01)
  *D06M 101/34* (2006.01)
  *D06M 101/38* (2006.01)

(52) U.S. Cl.
  CPC ............ *D06M 16/00* (2013.01); *D06M 23/06* (2013.01); *D06M 2101/32* (2013.01); *D06M 2101/34* (2013.01); *D06M 2101/38* (2013.01); *D10B 2331/02* (2013.01); *D10B 2331/04* (2013.01); *D10B 2331/06* (2013.01); *D10B 2331/12* (2013.01); *D10B 2401/13* (2013.01); *D10B 2509/022* (2013.01)

(56) References Cited

U.S. PATENT DOCUMENTS

| | | | |
|---|---|---|---|
| 5,271,998 | A | 12/1993 | Duckett |
| 5,955,175 | A | 9/1999 | Culler |
| 6,800,573 | B2 | 10/2004 | Van De Ven et al. |
| 6,824,819 | B2 | 11/2004 | Vogt et al. |
| 8,834,686 | B2 | 9/2014 | McClure et al. |
| 2003/0157147 | A1 | 8/2003 | Hoge et al. |
| 2006/0127462 | A1* | 6/2006 | Canada ............ A61P 17/02 442/128 |
| 2007/0203442 | A1 | 8/2007 | Bechert et al. |
| 2012/0276332 | A1 | 11/2012 | Conolly et al. |
| 2013/0299428 | A1* | 11/2013 | Bikel ............ B01D 67/009 427/244 |
| 2015/0291830 | A1 | 10/2015 | Galbreath et al. |

FOREIGN PATENT DOCUMENTS

| | | | |
|---|---|---|---|
| EA | 201201638 | A1 | 6/2014 |
| JP | H10-110257 | A * | 4/1998 |
| JP | H110257 | A | 4/1998 |
| JP | 2005290585 | A | 10/2005 |
| KR | 20090123445 | A | 12/2009 |
| WO | WO02070245 | A1 | 9/2002 |
| WO | WO03053484 | A1 | 7/2003 |
| WO | WO2006096098 | A2 | 9/2006 |
| WO | WO2006100480 | A1 | 9/2006 |
| WO | WO2013021409 | A1 | 2/2013 |

OTHER PUBLICATIONS

Yuranova, T., et al. "Antibacterial textiles prepared by RF-plasma and vacuum-UV mediated deposition of silver." Journal of Photochemistry and Photobiology A: Chemistry, vol. 161, No. 1, Nov. 17, 2003, pp. 27-34, https://doi.org/10.1016/s1010-6030(03)00204-1. (Year: 2003).*

"EA201201638A1_Machine Translation" is a machine translation of EA201201638A1. (Year: 2014).*

International Search Report Application No. PCT/US2020/031571, dated Jul. 20, 2020.

* cited by examiner

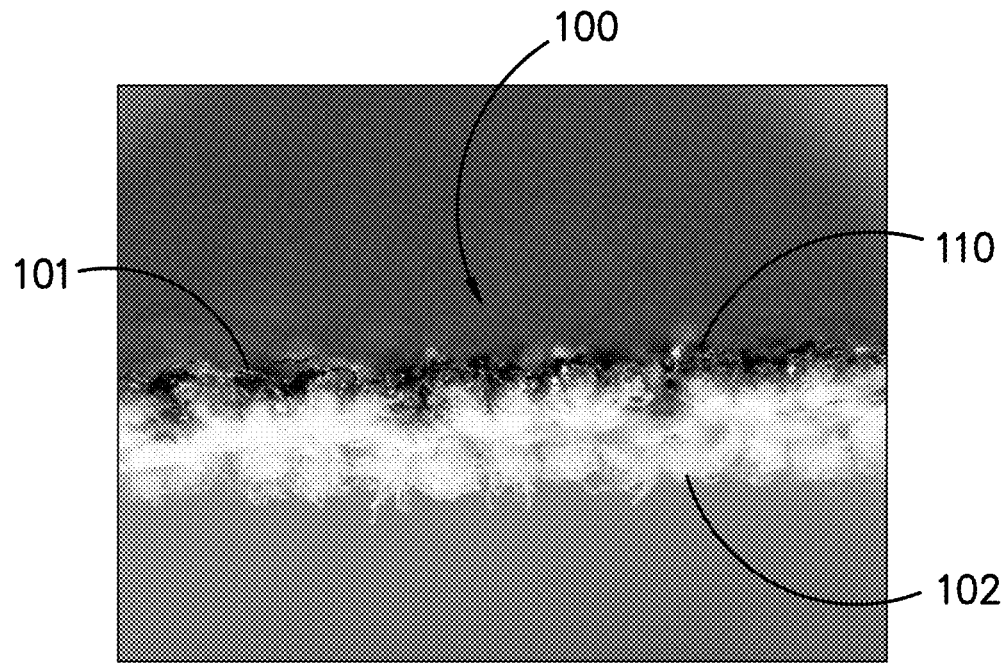
FIG. -1-
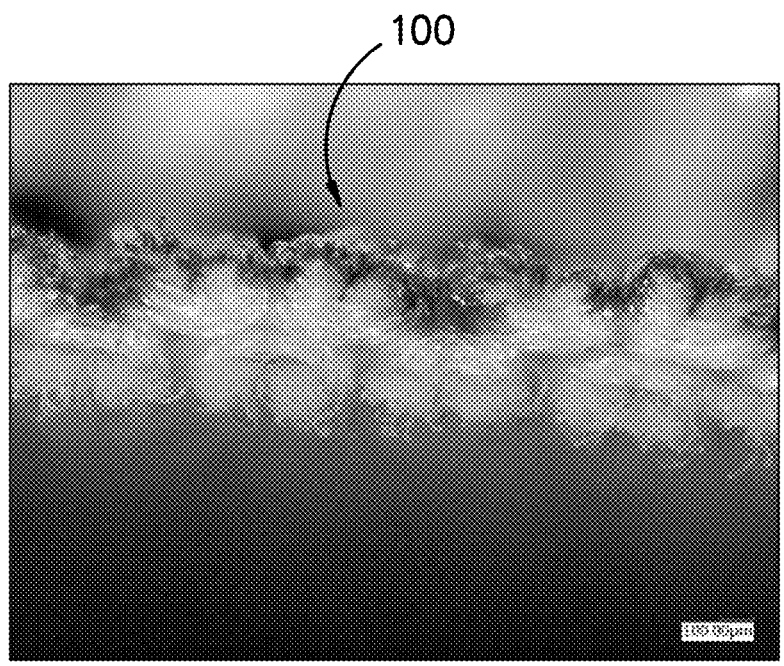
FIG. -2-

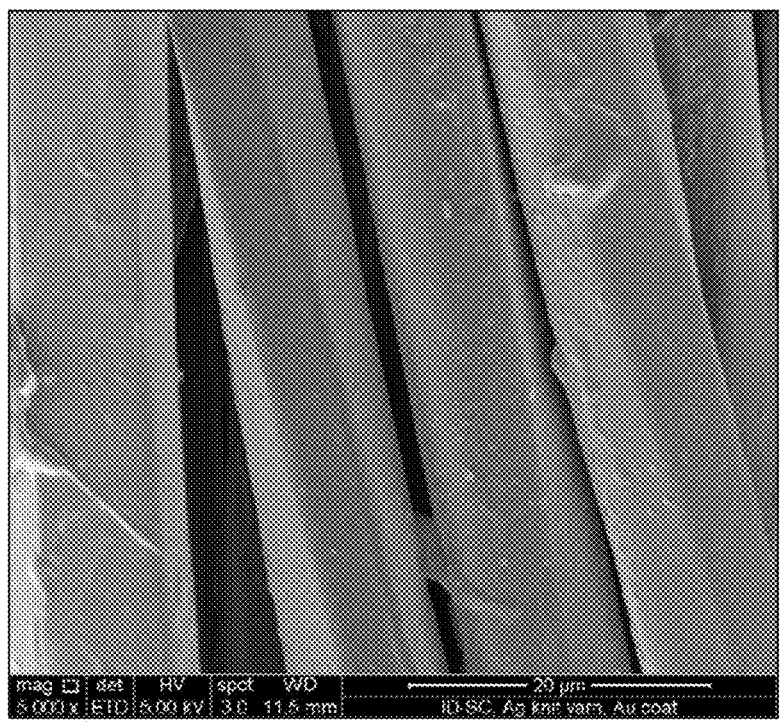
FIG. -3-
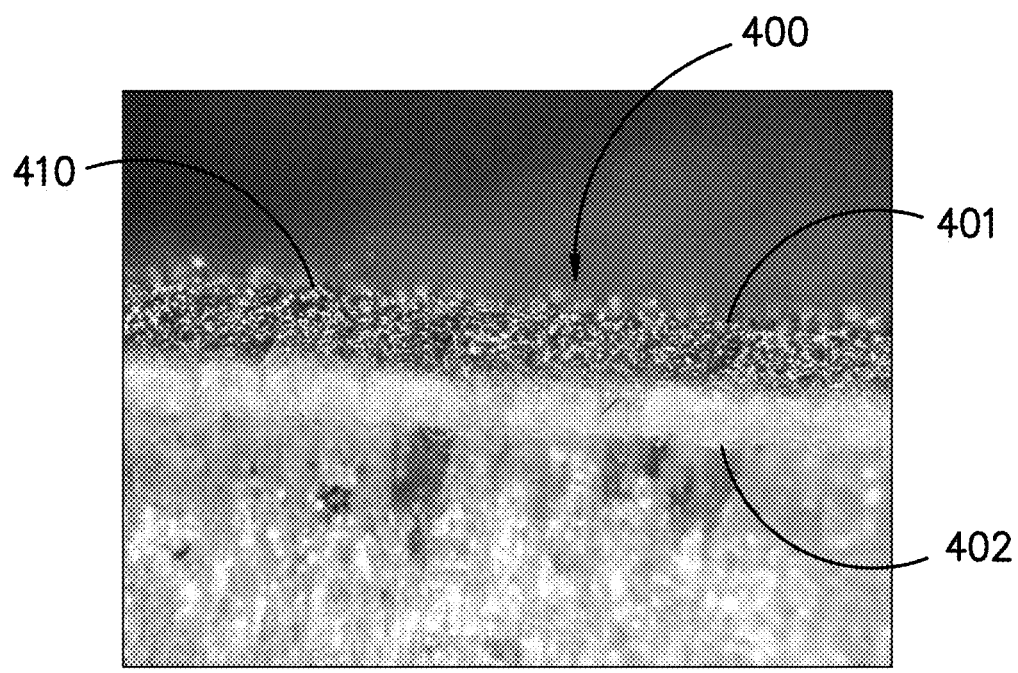
FIG. -4-

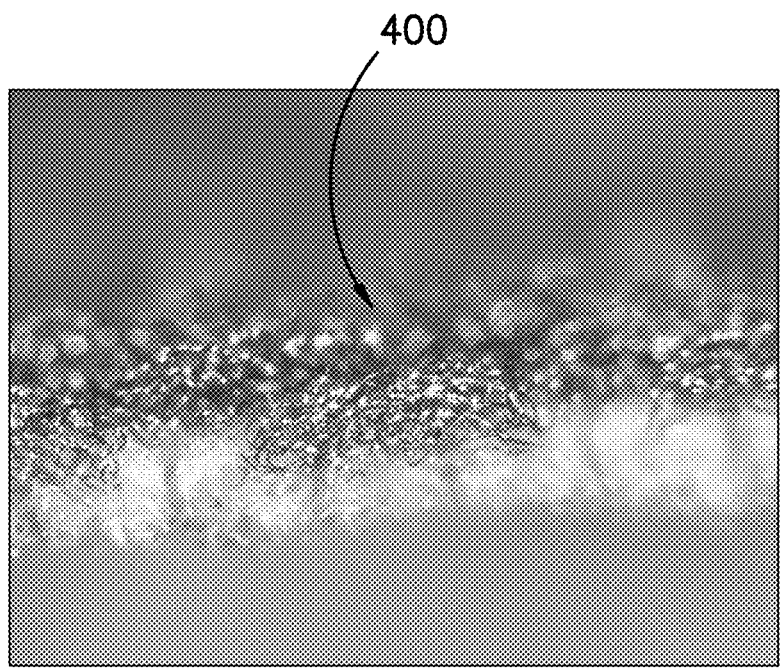
FIG. -5-
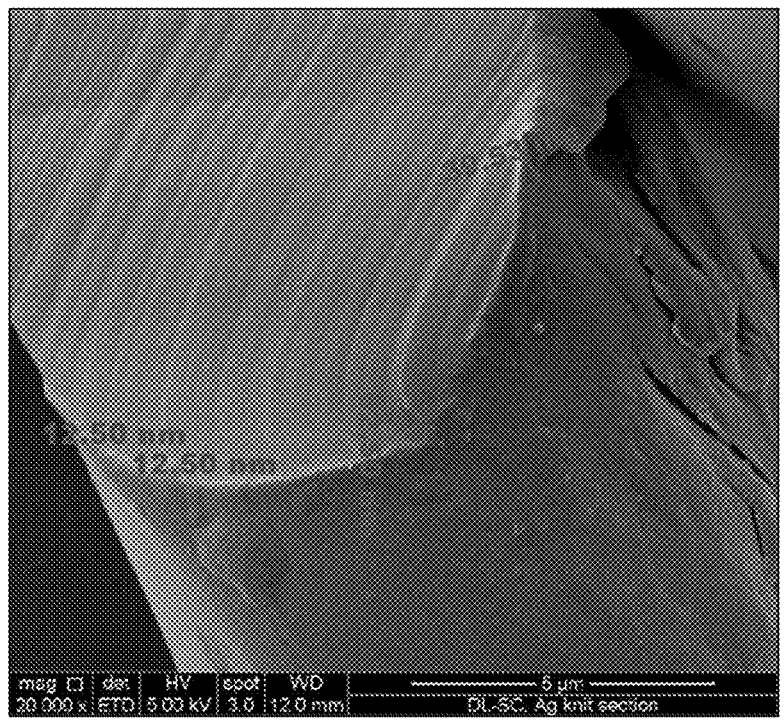
FIG. -6-

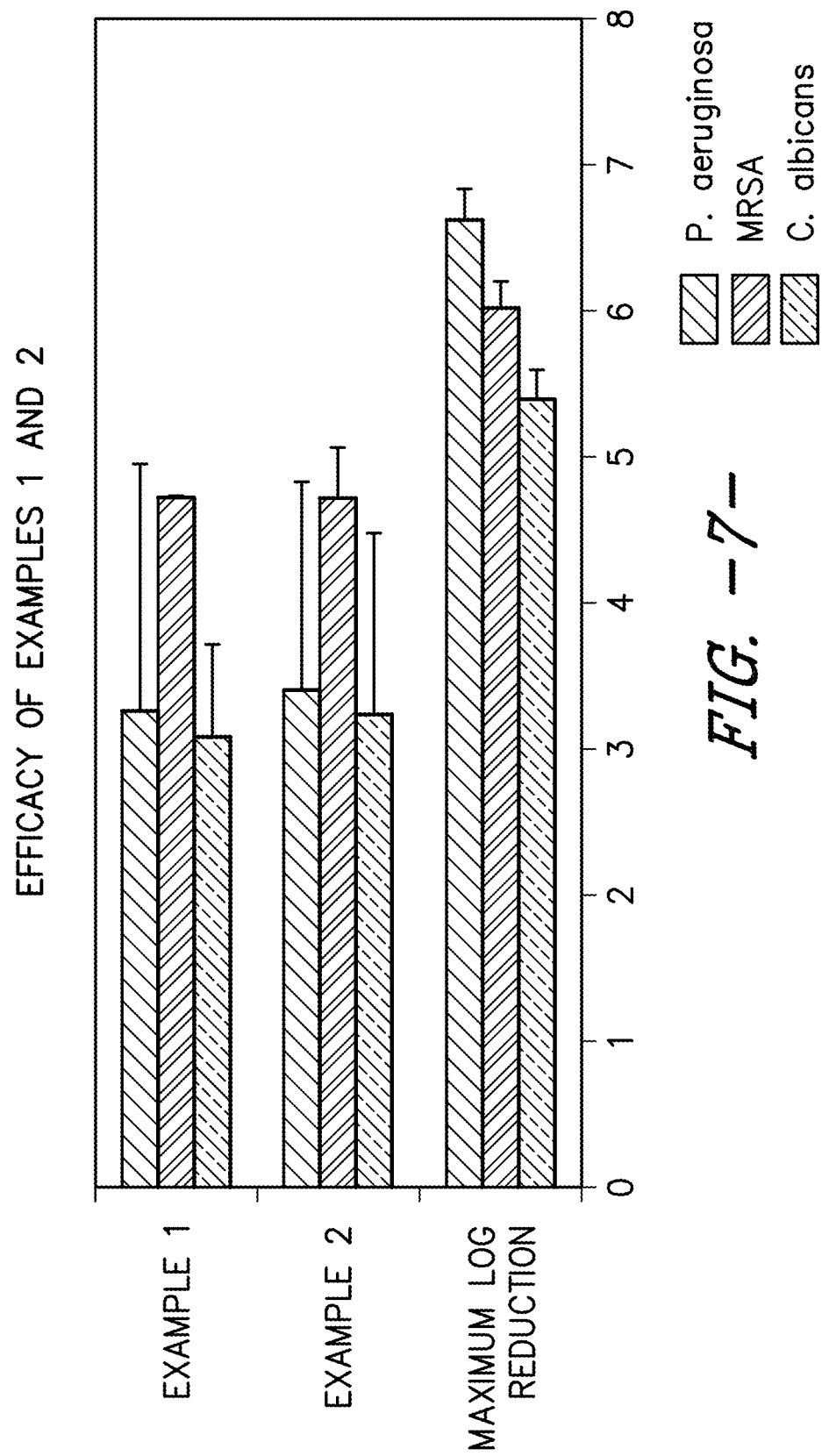
FIG. -7-

STAIN HIDING FABRIC WITH METALLIC COATING

CROSS REFERENCE TO RELATED APPLICATIONS

This application claims priority to U.S. Provisional Patent Application No. 62/851,683, entitled "Stain Hiding Fabric With Metallic Coating," which was filed on May 23, 2019, and is entirely incorporated by reference herein.

TECHNICAL FIELD

This invention relates to a method for hiding stains in medical dressings and other textile substrates. The method includes applying a metallic silver coating to a textile substrate via a plasma enhanced chemical vapor deposition (PECVP) process. The metallic silver coating effectively hides any stain that comes into direct contact with the treated substrate by transferring the liquid beneath the surface of the coating. The invention also relates to textile substrates containing metallic silver coatings.

BACKGROUND

There is a need for medical dressings for skin, wound and burn care that can hide stains. Stain release property upon washing is common for textile application, however, hiding stains of a textile material during application is uncommon. Even transparent liquids, such as water and sweat, change the optical property of the surface of a textile substrate and such liquids often result in visible staining. In this invention, polyester fabric (as one example) has been coated with a very thin layer of metallic silver using plasma enhanced chemical vapor deposition (PECVD) process, which has been demonstrated to hide the stain by transferring the liquid completely beneath the surface.

BRIEF SUMMARY

In one aspect, the invention relates to a stain hiding fabric comprised of a textile substrate having a wound contact surface and a non-wound contact surface, wherein the wound contact surface contains a metallized silver coating having a thickness in the range from 1% to 60%, based on the total thickness of the textile substrate.

In another aspect, the invention relates to a method for making a stain hiding fabric comprising the following steps: (a) providing a textile substrate having a wound contact and a non-wound contact surface, (b) exposing the wound contact surface of the textile substrate to a plasma enhanced chemical vapor deposition ("PECVD") process, and (c) allowing the PECVD process to add a metallic silver coating to the wound contact surface of the textile substrate.

In a further aspect, the invention relates to a method for hiding stains in a textile substrate comprising the following steps: (a) providing a textile substrate having a wound contact and a non-wound contact surface, (b) exposing the wound contact surface of the textile substrate to a plasma enhanced chemical vapor deposition ("PECVD") process, (c) allowing the PECVD process to add a metallic silver coating to the wound contact surface of the textile substrate to form a coated textile substrate, wherein the metallic silver coating has an exterior surface facing outward from the textile substrate and an interior surface facing inward to the textile substrate, (d) exposing the exterior surface of the metallic silver coating to an aqueous liquid, and (e) allowing the aqueous liquid to move from the exterior surface of the metallic silver coating to the interior surface of the metallic silver coating.

BRIEF DESCRIPTION OF THE DRAWINGS

FIG. 1 is a photomicrograph at 100× magnification of a polyester pique knit fabric (Example 1) containing a silver coating applied via a PECVD process.

FIG. 2 is a photomicrograph at 150× magnification of a polyester pique knit fabric (Example 1) containing a silver coating applied via a PECVD process.

FIG. 3 is a photomicrograph at 5000× magnification of a polyester pique knit fabric (Example 1) containing a silver coating applied via a PECVD process.

FIG. 4 is a photomicrograph at 50× magnification of a jersey knit fabric comprised of polyester, nylon and spandex fiber (Example 2) containing a silver coating on the primarily polyester surface of the fabric which was applied via a PECVD process.

FIG. 5 is a photomicrograph at 100× magnification of a jersey knit fabric comprised of polyester, nylon and spandex fiber (Example 2) containing a silver coating on the primarily polyester surface of the fabric which was applied via a PECVD process.

FIG. 6 is a photomicrograph at 20000× magnification of a single polyester fiber from the stain hiding fabric shown in FIGS. 4 and 5 (Example 2) containing a silver coating which was applied via a PECVD process.

FIG. 7 is a bar graph illustrating the antimicrobial efficacy of Examples 1 and 2.

DETAILED DESCRIPTION

The present invention described herein is a method for hiding stains in medical dressings and other textile substrates. The method includes applying a thin layer of silver to the surface of a textile substrate via plasma enhanced chemical vapor deposition ("PECVD"). Further, the invention includes textile substrates containing a surface coating of silver capable of effectively hiding stains encountered during use.

Liquids can interact with two main types of solid surfaces, high-energy solids and low-energy solids. The relative energy of a solid rely on the bulk nature of the solid itself. Solids such as metals, glasses, and ceramics are known as 'hard solids' because the chemical bonds that hold them together are very strong. Thus, it takes a large input of energy to break these solids (alternatively large amount of energy is required to cut the bulk and make two separate surfaces so high surface energy), so they are termed "high energy." Most molecular liquids achieve complete wetting with high-energy surfaces. In case of good quality conformal metallic coating, any underlying materials is almost isolated and thus will have very limited absorbency of any liquid. With good quality metal coating, it has been discovered that excellent wetting, with a limited absorbency surface, can be achieved and transfers any liquid underneath the surface very efficiently and effectively hides the stain.

In the specific case of textile materials, solids are weak molecular crystals where the molecules are held together essentially by physical forces (e.g., van der Waals and hydrogen bonds). Since these solids are held together by weak forces, a very low input of energy is required to break them, thus they are termed "low energy." Depending on the type of liquid chosen, low-energy surfaces can permit either complete or partial wetting. Since these materials have high absorbency, they tend to absorb and hold a large quantity on liquid on the surface.

The process of plasma enhanced chemical vapor deposition is known for applying coatings to surfaces of substrates such as, for example, in semiconductors and high-performance optical glass applications. Typically, these substrates are non-porous in nature. In contrast, the invention described herein is using the PECVD process to apply a metallic silver coating to porous substrates, such as textile substrates.

The PECVD process is disclosed in US Patent Application Publication No. 2015/0291830 to Galbreath et al., which is entirely incorporated by reference herein. In one aspect of the present invention, only one side of the textile substrate is treated via PECVD. Thus, only one side of the treated textile substrate (the wound facing side or wound contact side) contains a metallic silver coating. As a result, one surface of the treated textile substrate (the non-wound facing side) is free from metallic silver (i.e. the non-wound facing side does not contain silver and has not been treated with PECVD).

The term "metallic' is intended to include elemental metals and compounds thereof. In one aspect of the invention, metallic silver is coated onto the surface of a textile substrate. The source of silver for deposition onto the textile substrate includes aqueous solutions of silver salt (such as silver nitrate), silver oxide, silver nanoparticles, or other silver-containing compounds. In one aspect of the invention, silver ions (e.g. $Ag^+$) are reduced to silver (e.g. $Ag^0$) according to known reactions and applied as a coating to the surface of a substrate. On average, the silver coating is present on the fibers at the surface of the textile substrate in a range from about 200 to 300 angstroms, i.e. 20 nm to 30 nm.

Textile substrates include materials selected from synthetic fiber, natural fiber, man-made fiber using natural constituents, inorganic fiber, glass fiber, and a blend of any of the foregoing. By way of example only, synthetic fibers may include polyester, acrylic, polyamide, polyolefin, polyaramid, polyurethane, or blends thereof. More specifically, polyester may include polyethylene terephthalate, polytrimethylene terephthalate, polybutylene terephthalate, polylactic acid, or combinations thereof. Polyamide may include nylon 6, nylon 6,6, or combinations thereof. Polyolefin may include polypropylene, polyethylene, or combinations thereof. Polyaramid may include poly-p-phenyleneteraphthalamide (i.e., Kevlar®), poly-m-phenyleneteraphthalamide (i.e., Nomex®), or combinations thereof. Exemplary natural fibers include wool, cotton, linen, ramie, jute, flax, silk, hemp, or blends thereof. Exemplary man-made materials using natural constituents include regenerated cellulose (i.e., rayon), lyocell, or blends thereof.

The material comprising the textile substrate may be formed from staple fiber, filament fiber, slit film fiber, or combinations thereof. The fiber may be exposed to one or more texturing processes. The fiber may then be spun or otherwise combined into yarns, for example, by ring spinning, open-end spinning, air jet spinning, vortex spinning, or combinations thereof. Accordingly, the textile substrate will generally be comprised of interlaced fibers, interlaced yarns, loops, or combinations thereof.

The textile substrate may be comprised of fibers or yarns of any size, including microdenier fibers or yarns (fibers or yarns having less than one denier per filament). The fibers or yarns may have deniers that range from less than about 0.1 denier per filament to about 2000 denier per filament or, more preferably, from less than about 1 denier per filament to about 500 denier per filament.

Further, the textile substrate may be partially or wholly comprised of multi-component or bi-component fibers or yarns in various configurations such as, for example, islands-in-the-sea, core and sheath, side-by-side, or pie configurations. Depending on the configuration of the bi-component or multi-component fibers or yarns, the fibers or yarns may be splittable along their length by chemical or mechanical action.

Additionally, the fibers and/or yarns may include additives coextruded therein, may be precoated with any number of different materials, including those listed in greater detail below, and/or may be dyed or colored to provide other aesthetic features for the end user with any type of colorant, such as, for example, poly(oxyalkylenated) colorants, as well as pigments, dyes, tints, and the like. Other additives may also be present on and/or within the target fiber or yarn, including antistatic agents, brightening compounds, nucleating agents, antioxidants, UV stabilizers, fillers, permanent press finishes, softeners, lubricants, curing accelerators, and the like. The fibers and/or yarns comprising the textile substrate may be dyed or undyed. If the fibers are dyed, they may be solution dyed. The weight and density of textile substrate will vary depending on the desired aesthetics and performance requirements of its intended end-use.

The textile substrate may be selected from the group consisting of woven material, nonwoven material, knitted material, and combinations thereof.

Turning to the Figures, FIG. 1 is a photomicrograph at 100× magnification of one embodiment of stain hiding fabric 100. Stain hiding fabric 100 is comprised of 100% polyester fiber in a pique knit construction and contains silver coating 110 on wound facing surface 101 of the fabric. As illustrated in the photomicrograph, non-wound facing surface 102 of stain hiding fabric 100 does not contain silver coating 110. FIG. 2 is a photomicrograph at 150× magnification of stain hiding fabric 100 shown in FIG. 1.

FIG. 3 is a photomicrograph at 5000× magnification of stain hiding fabric 100 shown in FIGS. 1 and 2. FIG. 3 further illustrates the silver coating present on the individual fibers of wound facing surface 101 of the fabric.

FIG. 4 is a photomicrograph at 50× magnification of another embodiment of the invention. FIG. 4 shows stain hiding fabric 400. Stain hiding fabric 400 is comprised of 21% polyester fiber, 65% nylon fiber, and 14% spandex fiber in a jersey knit construction and contains silver coating 410 on wound facing surface 401 of the fabric. The wound facing surface of fabric 400 is comprised primarily of polyester fiber. As illustrated in the photomicrograph, non-wound facing surface 402 of stain hiding fabric 400 does not contain silver coating 410. Non-wound facing surface 402 is comprised primarily of nylon fiber. FIG. 5 is a photomicrograph at 100× magnification of stain hiding fabric 400 shown in FIG. 4. FIG. 6 is a photomicrograph at 20,000× magnification of a single polyester fiber coated of stain hiding fabric 400 of FIGS. 4 and 5. Silver coating 410 is visible on the surface of the polyester fiber. Measurements are provided illustrating the thickness of silver coating 410.

Stain hiding fabric 400 includes wound facing surface 401 comprising a metallized silver coating having a thickness in the range from 1% to 60%, or from 5% to 40%, or from 10% to 35%, or from 20% to 40%, based on the total thickness of the fabric. The fiber content of stain hiding fabric 400 may also be as follows: 15% to 30% polyester fiber, 55% to 75% nylon fiber, and 10% to 20% spandex fiber.

With respect to the metallic silver coating, it is noted that the coating is a conformal coating as is known to those skilled in the art of metal coatings. Conformal coatings are typically very thin coatings applied to surfaces. The SEM image included as FIGS. 3 and 6 clearly illustrate the conformal metallic silver coating of the present invention. The metallic silver coating is not comprised of metal particles on the surface of the textile substrate of fibers comprising the textile substrate.

EXAMPLES

The invention may be further understood by reference to the following examples which are not to be construed as limiting the scope of the present invention.

Two fabrics were evaluated for stain hiding properties. Example 1 was a 100% polyester pique knit fabric. One side of Example 1 was coated with metallic silver using the PECVD process. The surface that was coated with metallic silver was the surface intended to be the wound facing (or wound contact) surface of the fabric.

Example 2 was a jersey knit fabric comprised of 21% polyester fiber, 65% nylon fiber, and 14% spandex fiber. Based on its knit construction, one surface of Example 1 was primarily comprised of polyester fiber, and the opposite surface was comprised of primarily nylon fiber. The surface comprised primarily of polyester fiber was coated with metallic silver using the PECVD process. The surface that was coated with metallic silver was the surface intended to be the wound facing (or wound contact) surface of the fabric.

Additional details regarding samples tested are shown in Table 1 below:

Simulated wound fluid ("SWF") was prepared by adding 16.60 g NaCl and 0.56 g $CaCl_2$ to a 2 L volumetric flask. The flask was then filled to volume (2000 mL total) with deionized water. The flask was then capped and shaken until all of the salts were completely dissolved. The simulated wound fluid is comprised of 0.142M (142 mM) NaCl (aq) and 0.0025M (2.5 mM) $CaCl_2$ (aq).

Several drops of each fluid preparation were added to the surface of each sample. Each sample was then visually evaluated for its ability to hide stains.

Based on qualitative assessment, the stain hiding property of Example 2 was greater than Example 1. In addition, the stain hiding property of Example 1 was better than all of the Control samples.

The knit constriction of Example 1 was different from Example 2. The fabric of Example 1 was equally dense with the yarns on both, face and back. The polyester side of Example 2 contained fluffy, low-density loops. Thus, when the metallic silver was coated on the low-density side, with even lower loading of silver (1562 ppm of silver in Example 2 vs. 2242 ppm of silver in Example 1), thickness coverage with silver coating for Example 2 (37.3%) was significantly higher than that of Example 1 (21.2%). Scanning electron microscopy ("SEM")/energy dispersive spectroscopy ("EDS") analysis confirmed the presence of silver on the wound contact/wound facing side of the fabric and no silver on the non-wound contact/non-wound facing side of the fabric.

Examples 1 and 2 were tested for antimicrobial efficacy against Gram positive bacteria (e.g. methicillin resistant

TABLE 1

Fabrics Evaluated for Stain Hiding Properties

| Sample | Component | Fabric Construction | Silver Content (ppm) | Thickness of the Fabric (mm) | Thickness Coated with Silver (mm) | % Coated with Silver |
|---|---|---|---|---|---|---|
| Example 1 | Undyed Polyester | Pique knit | 2242 | 0.42 | 0.090 | 21.2% |
| Control 1 | Undyed Polyester | Pique knit | n/a | 0.42 | n/a | n/a |
| Example 2 | Undyed Polyester Nylon Spandex | Jersey knit | 1562 | 0.80 | 0.336 | 37.3% |
| Control 2 | Undyed Polyester Nylon Spandex | Jersey knit | n/a | 0.80 | n/a | n/a |
| Control 3 | Disperse Dyed Polyester | Pique knit | n/a | 0.42 | n/a | n/a |

All samples were evaluated for stain hiding properties. Control samples were also prepared and evaluated. Control 1 was the same as Example 1, except without the silver coating. Control 2 was the same as Example 2, except without the silver coating. Each sample was exposed to simulated wound fluid ("SWF") that contained no dye, SWF containing red dye, and SWF containing blue dye.

*Staphylococcus aureus*, "MRSA") and Gram negative bacteria (e.g. *Pseudomonas aeruginosa*). They were also tested for antifungal efficacy (e.g. *Candida albicans*). Examples 1 and 2 exhibited good antimicrobial efficacy against both Gram positive and Gram negative bacteria and good antifungal efficacy. Test result are provided in Table 2 and FIG. 7.

TABLE 2

Antimicrobial and Antifungal Efficacy of Example 1 and Example 2

| Sample | P. aeruginosa | | MRSA | | C. albicans | |
|---|---|---|---|---|---|---|
| | Average Log Reduction | Standard Deviation | Average Log Reduction | Standard Deviation | Average Log Reduction | Standard Deviation |
| Initial Bioburden | 9.89E+05 | | 4.99E+06 | | 4.99E+06 | |
| Internal Untreated Control | −2.58 | 0.21 | −1.27 | 0.18 | −0.65 | 0.20 |
| Example 1 | 3.26 | 1.70 | 4.72 | 0.01 | 3.08 | 0.63 |
| Example 2 | 3.40 | 1.43 | 4.72 | 0.35 | 3.23 | 1.25 |
| Maximum Log Reduction | 6.62 | 0.21 | 6.02 | 0.18 | 5.40 | 0.20 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

We claim:

1. A stain hiding fabric consisting of a textile substrate in the form of a knit fabric having a wound contact surface and a non-wound contact surface, wherein the wound contact surface contains a metallized silver coating having a thickness in the range from 1% to 60%, based on the total thickness of the textile substrate, and wherein the metallized silver coating is present on an outermost surface of the stain hiding fabric directly in contact with a wound.

2. The stain hiding fabric of claim 1, wherein the metallized silver coating has a thickness in the range from 5% to 40%, based on the total thickness of the textile substrate.

3. The stain hiding fabric of claim 1, wherein the wound contact surface is comprised of fibers containing the metallized silver coating of less than 100 nm.

4. The stain hiding fabric of claim 1, wherein the wound contact surface is comprised of fibers containing the metallized silver coating in the range from 20 nm to 30 nm.

5. The stain hiding fabric of claim 1, wherein the knit fabric is a pique knit fabric.

6. The stain hiding fabric of claim 1, wherein the knit fabric is a circular knit fabric.

7. The stain hiding fabric of claim 6, wherein the circular knit fabric is a jersey knit fabric.

8. The stain hiding fabric of claim 1, wherein the textile substrate is comprised of 15% to 30% polyester fiber, 55% to 75% nylon fiber, and 10% to 20% spandex fiber.

9. The stain hiding fabric of claim 1, wherein the textile substrate is comprised of 100% polyester fiber.

10. The stain hiding fabric of claim 1, wherein the textile substrate is comprised of a blend of polyester and nylon fiber.

11. The stain hiding fabric of claim 7, wherein the blend further includes spandex fiber.

12. The stain hiding fabric of claim 1, wherein the metallic silver is a conformal coating.

13. The stain hiding fabric of claim 1, wherein the fabric exhibits antimicrobial efficacy against Gram positive and Gram negative bacteria.

14. The stain hiding fabric of claim 1, wherein the fabric exhibits antifungal efficacy.

* * * * *